(12) United States Patent
Itoh

(10) Patent No.: US 6,598,970 B2
(45) Date of Patent: Jul. 29, 2003

(54) OPHTHALMOLOGIC APPARATUS

(75) Inventor: Hiroshi Itoh, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 155 days.

(21) Appl. No.: 09/813,127

(22) Filed: Mar. 21, 2001

(65) Prior Publication Data

US 2001/0028439 A1 Oct. 11, 2001

(30) Foreign Application Priority Data

Mar. 31, 2000 (JP) .......................................... 2000-098625

(51) Int. Cl.⁷ ................................................. A61B 3/14
(52) U.S. Cl. ..................................................... 351/206
(58) Field of Search ................................ 600/476, 479, 600/504; 351/208, 211, 205, 206, 221

(56) References Cited

U.S. PATENT DOCUMENTS 5,163,437 A  11/1992 Fuji et al. .................... 128/665
6,193,372 B1 * 2/2001 Okumura et al. ............ 351/221
6,411,839 B1 * 6/2002 Okinishi ...................... 600/479

* cited by examiner

Primary Examiner—George Manuel
(74) Attorney, Agent, or Firm—Fitzpatrick, Cella, Harper & Scinto

(57) ABSTRACT

An ophthalmologic apparatus includes a measuring system for measuring a blood vessel in fundus of an eye to be examined, an image pickup system for performing image pickup of the eye fundus together with information representing a measurement position in the measuring system, a switch for allowing an operator to operate, and a control system. The control system controls to start measurement by the measuring system by operation of the switch as a trigger. Then, when the operator operates extra operation for the switch, the control system controls to execute the image pickup, otherwise the control system controls not to execute the image pickup.

20 Claims, 5 Drawing Sheets

FIG. 3A
FIG. 3B
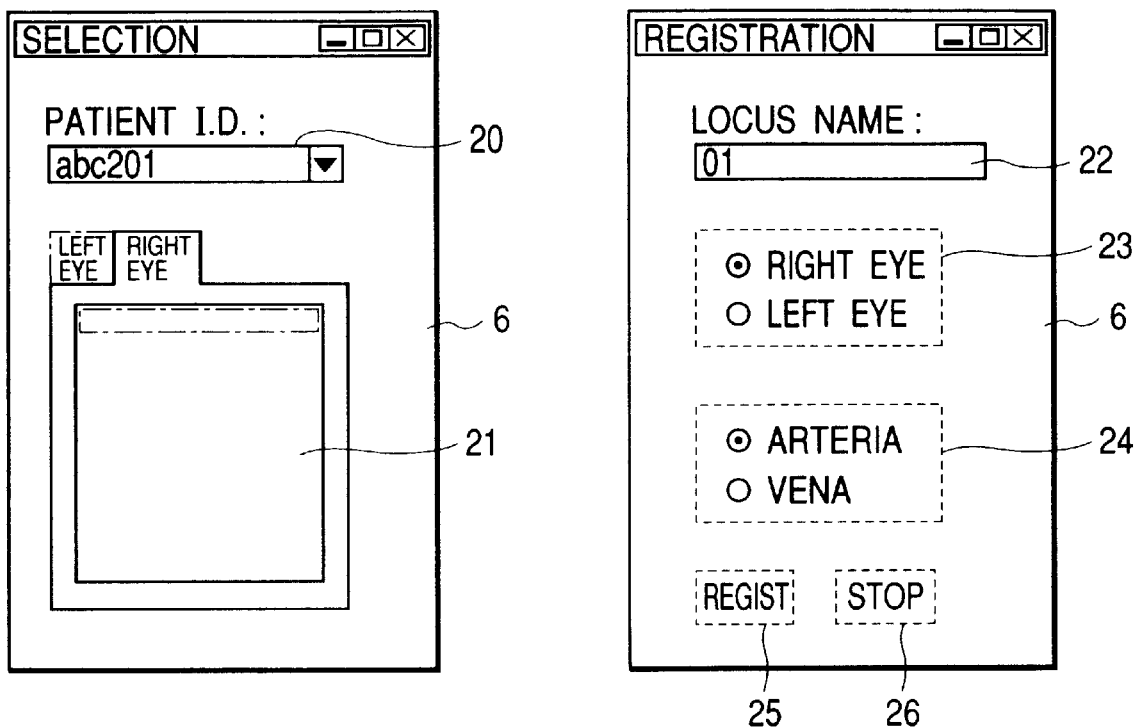
FIG. 4
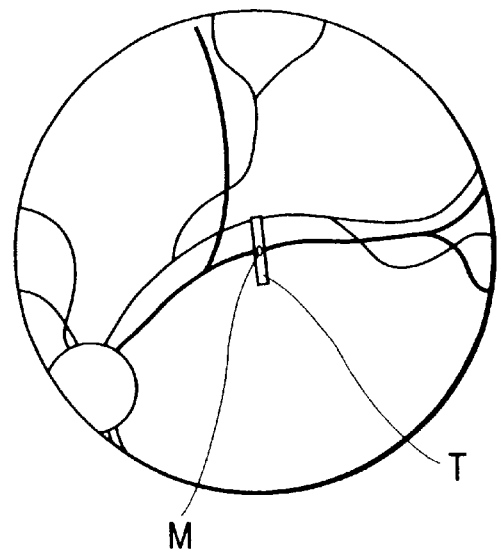

FIG. 5
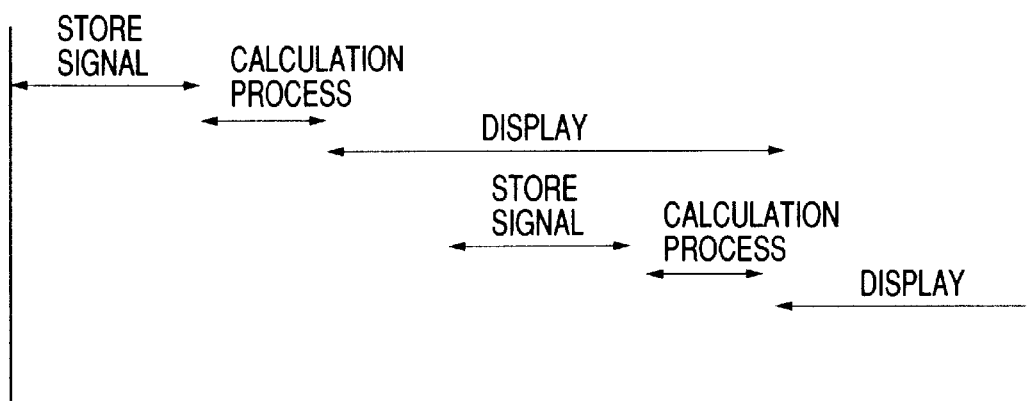
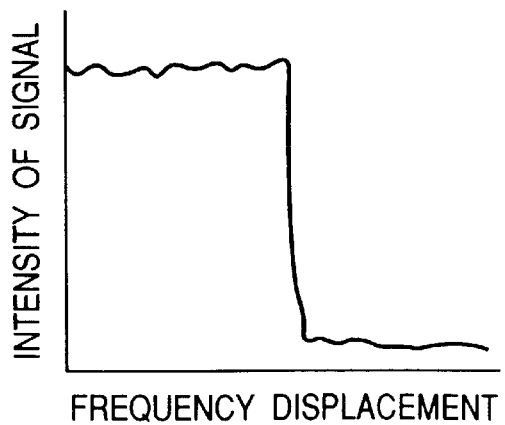
FIG. 6A
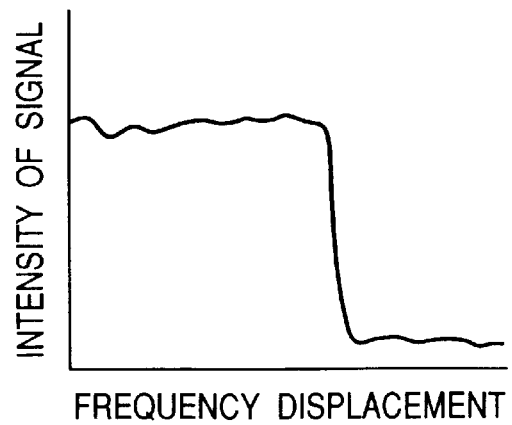
FIG. 6B

OPHTHALMOLOGIC APPARATUS

BACKGROUND OF THE INVENTION

1. Field of the Invention

The present invention relates to a system for performing measurement of an eye fundus vascular blood flow velocity of a patient's eye and eye fundus image pickup in an ophthalmic hospital or the like.

2. Related Background Art

In an eye fundus blood flowmeter, an example of an ophthalmologic apparatus, when a locus of a blood vessel on a retina is measured, it is preferred that an eye fundus image be stored together with information representing the measurement locus. This is preferable because, in comparison with handwriting of a measurement position, such storing alleviates errors and, stored contents are visually easy to understand. Further it is useful in a case where an identical locus is again measured later. Thus, considering eye movement and flicks of a patient, it is desired that image pickup is performed almost simultaneously with measurement in order to improve reliability of an eye fundus image.

As shown in U.S. Pat. No. 5,163,437, a system in which a chart representing a measurement range is disposed optically in conjugate with the eye fundus and which performs image pickup of an eye fundus image together with the chart almost simultaneously with the start of measurement when a measurement switch is pushed has been known. However, in this system, when the measurement is performed by pushing the measurement switch, the image pickup is necessarily performed. Thus, even when the operator does not desire, the image pickup may be performed. Such unnecessary image pickup causes complication in data reduction and diagnosis, which are made later. In addition, this causes the increase in unnecessary consumption of memory area in a storage device.

SUMMARY OF THE INVENTION

A main object of the present invention is to provide a further improvement of an eye fundus blood flowmeter. For example, one concrete object example is to provide an ophthalmologic apparatus in which unnecessary image pickup as mentioned above can be prevented. A further object of the present invention is to provide an ophthalmologic apparatus which is a system capable of performing both measurement and image pickup and in which the image pickup can be canceled by the operator's will.

To attain the above object, according to one aspect of the present invention, there is provided an ophthalmologic apparatus comprising:

a measuring system for measuring a blood vessel of an eye fundus of an eye to be examined;

an image pickup system for performing image pickup of the eye fundus together with information representing a measurement position in the measuring system;

a switch for allowing an operator to operate; and a control system for controlling to start measurement by the measuring system by operation of the switch as a trigger, and then controlling to execute the image pickup when the operator operates extra operation for the switch, otherwise not to execute the image pickup.

According to one aspect of the present invention, there is preferably provided an ophthalmologic apparatus, characterized in that the switch has a push button, and the control system controls:

to execute the measurement when the operator pushes the push button; and then to execute the image pickup when the operator continuously pushes the push button for a period longer than a predetermined period, otherwise to cancel the image pickup.

According to one aspect of the present invention, there is preferably provided an ophthalmologic apparatus, characterized in that the switch has a push button, and the control system controls:

to execute the measurement when the operator pushes the push button once; and then to execute the image pickup when the operator pushes the push button plural times in succession, otherwise to cancel the image pickup.

According to one aspect of the present invention, there is preferably provided an ophthalmologic apparatus, characterized in that the switch has a push button, and the control system controls:

to execute the measurement when the operator pushes the push button; and then to execute the image pickup when the operator again pushes the push button within a predetermined period, otherwise to cancel the image pickup.

According to one aspect of the present invention, there is preferably provided an ophthalmologic apparatus, characterized in that the switch has a first switch and a second switch, and the control system executes the measurement by the first switch as a trigger, and executes the image pickup by the second switch as a trigger.

According to one aspect of the present invention, there is preferably provided an ophthalmologic apparatus, characterized in that the switch has a double-action-switch in which the first switch and the second switch are turned on in order by a single push button.

According to one aspect of the present invention, there is preferably provided an ophthalmologic apparatus, characterized in that the measuring system includes a tracking system for performing tracking of the blood vessel, and the information representing the measurement position is an image of, a measurement beam or a tracking beam.

According to one aspect of the present invention, there is preferably provided an ophthalmologic apparatus, characterized in that the switch has a double-action-switch in which a first switch and a second switch are turned on in order by a single push button, and the control system executes the tracking by the tracking system using the first switch as a trigger, and executes the measurement using the second switch as a trigger.

According to one aspect of the present invention, there is preferably provided an ophthalmologic apparatus, further comprising:

a registering system for registering an identifier inherent to each measurement position; and a storage device for storing an image of the eye fundus, which is taken by the image pickup system, in relation to the identifier.

According to one aspect of the present invention, there is preferably provided an ophthalmologic apparatus, characterized in that the storage device stores the taken image together with a measurement result measured by the measuring system, in relation to the identifier.

According to another aspect of the present invention, there is provided an ophthalmologic apparatus comprising:

a measuring system for measuring a blood vessel of an eye fundus of an eye to be examined;

an image pickup system for performing image pickup of the eye fundus together with information representing a measurement position in the measuring system;

a switch for allowing an operator to operate; and a control system for controlling to execute measurement by the measuring system and the image pickup by the image pickup system using operation of the switch by the operator as a trigger, the control system controlling to cancel the image pickup in some cases.

According to another aspect of the present invention, there is preferably provided an ophthalmologic apparatus, characterized in that the control system does not perform canceling of the image pickup when a measurement position is for first measurement, otherwise allows the canceling.

According to another aspect of the present invention, there is preferably provided an ophthalmologic apparatus, characterized in that the control system controls to execute the image pickup when the operator operates extra operation for the switch, otherwise to cancel the image pickup.

According to another aspect of the present invention, there is preferably provided an ophthalmologic apparatus, characterized in that the control system does not cancel the image pickup when a measurement position is for first measurement.

According to another aspect of the present invention, there is preferably provided an ophthalmologic apparatus, characterized in that the measuring system includes a tracking system for performing tracking of the blood vessel, and the information representing the measurement position is an image of, a measurement beam or a tracking beam.

According to another aspect of the present invention, there is preferably provided an ophthalmologic apparatus further comprising:

a registering system for registering an identifier inherent to each measurement position; and a storage device for storing an image of the eye fundus, which is taken by the image pickup system, in relation to the identifier.

According to another aspect of the present invention, there is preferably provided an ophthalmologic apparatus, characterized in that the storage device stores the taken image together with a measurement result measured by the measuring system, in relation to the identifier.

According to another aspect of the present invention, there is provided an ophthalmologic apparatus comprising:

a measuring system for measuring a blood vessel of an eye fundus of an eye to be examined;

an image pickup system for performing image pickup of the eye fundus together with information representing a measurement position in the measuring system;

a registering system for registering an inherent identifier corresponding to a measurement position; and a storage device for storing an image of the eye fundus, which is taken by the image pickup system, in relation to the identifier.

According to another aspect of the present invention, there is preferably provided an ophthalmologic apparatus, characterized in that the storage device stores the taken image together with a measurement result measured by the measuring system, in relation to the identifier.

According to another aspect of the present invention, there is preferably provided an ophthalmologic apparatus, characterized in that when a plurality of image pickups are performed, the storage device deletes a preceding image and stores a current image.

According to another aspect of the present invention, there is preferably provided an ophthalmologic apparatus, characterized in that while the measurement result by the measuring system is stored in the storage device, the image pickup of the eye fundus is started.

According to another aspect of the present invention, there is preferably provided an ophthalmologic apparatus, characterized in that the image pickup of the eye fundus is started almost simultaneously with the start of storing of the measurement result by the measuring system into the storage device.

According to another aspect of the present invention, there is preferably provided an ophthalmologic apparatus, characterized in that the image pickup of the eye fundus is started almost simultaneously with completion of storing of the measurement result by the measuring system into the storage device.

Further objects of the present invention and embodiments thereof are clear in description of the embodiments below.

BRIEF DESCRIPTION OF THE DRAWINGS

FIGS. 3A and 3B are screen display examples for inputting an examination locus;

FIG. 4 is an explanatory diagram of an eye fundus image when measurement light is projected;

FIG. 5 is a time chart representing a sequence of signals during trial measurement;

FIGS. 6A and 6B are graphs representing the states that FFT signals are good, FIG. 6A represents a signal from a first photomultiplier and FIG. 6B represents a signal from a second photomultiplier;

DESCRIPTION OF THE PREFERRED EMBODIMENTS

Figure 1:
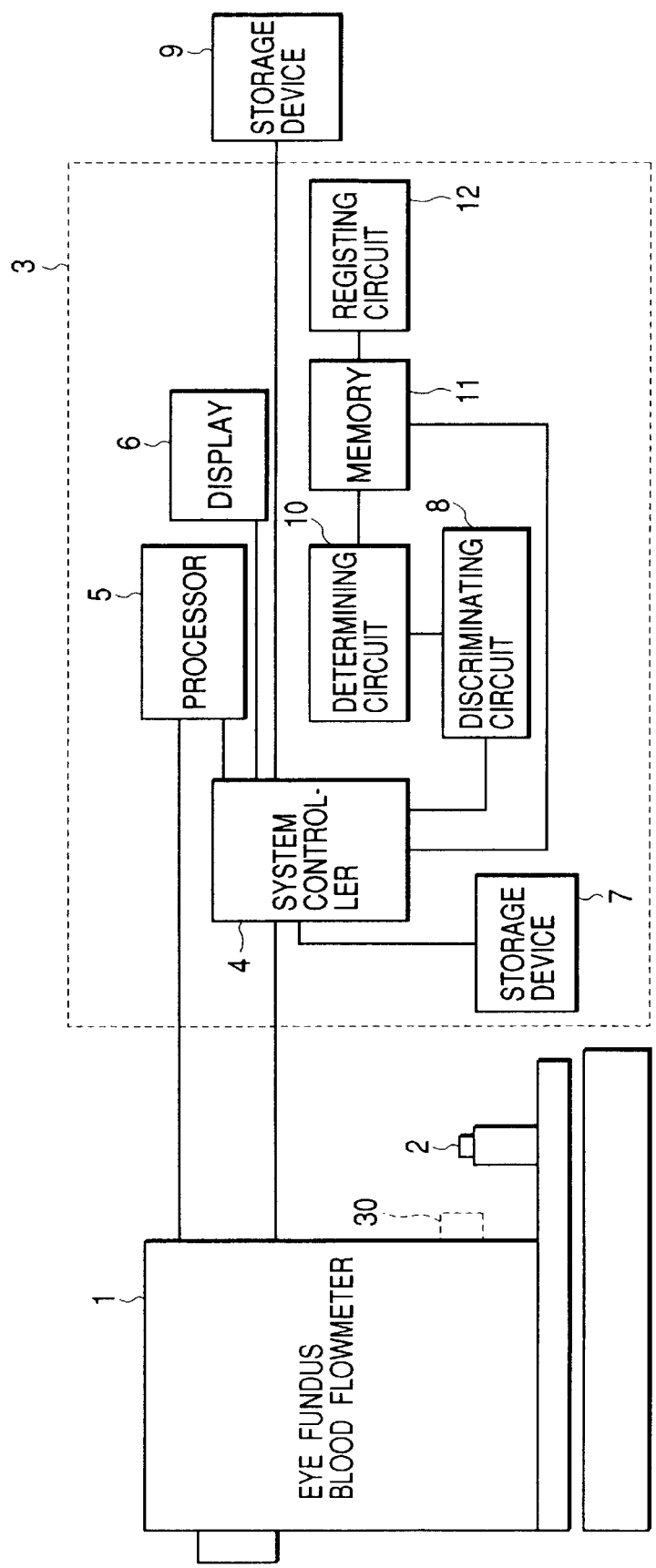
FIG. 1 is a block diagram of the entire system of an eye fundus blood flowmeter.

FIG. 1 is a block diagram of a system of an eye fundus blood flowmeter to which the present invention is applied. The eye fundus blood flowmeter 1 roughly includes an image pickup system for photo-taking an eye fundus image together with a mark (an image of, measurement beam or tracking beam) for indicating a measurement position, and a tracking system for tracking flicks of a patient (a person to be examined). In this operation, an operation device 2 with a double-action-switch is used as a measurement switch. This double-action-switch has a single push button. When an operator pushes this push button lightly, a first-action switch is turned on. After further pushing, a second-action switch is turned on. This is provided on a head portion of a joystick for alignment.

The operation of the eye fundus blood flowmeter 1 is controlled by a computer system 3. The computer system 3 for the eye fundus blood flowmeter 1 includes a system controller 4 for performing control of the entire apparatus such as determination of whether image pickup is allowed or not, and a processor 5. The processor 5 analyzes a signal with respect to a blood flow velocity, which is outputted by measurement of the eye fundus blood flowmeter 1, and performs calculation for producing an intermediate result such that whether measurement is good or bad can be determined. The computer system 3 further includes a display 6, a storage device 7, a discriminating circuit 8, a determining circuit 10, a memory 11 and a registering circuit 12. The discriminating circuit 8 discriminates a measurement position. The determining circuit 10 determines next measurement position when one measurement position is selected from measurement positions which have been registered. The memory 11 stores data representing whether measurement in the registered measurement position has already been performed or not. The registering circuit 12 registers identifiers which do not duplicate for measurement positions before the start of examination. Further, an external storage device 9 (CD-ROM, MO, HDD, or the like) is provided such that it can be accessed from the computer system 3.

When the computer system 3 is operated, the processor 5 executes software. This software is stored in the storage device 9. Alternatively, an application software is stored in a server on a medical network with which the eye fundus camera is connected, and the processor may read the stored application software and execute it.

Figure 2:
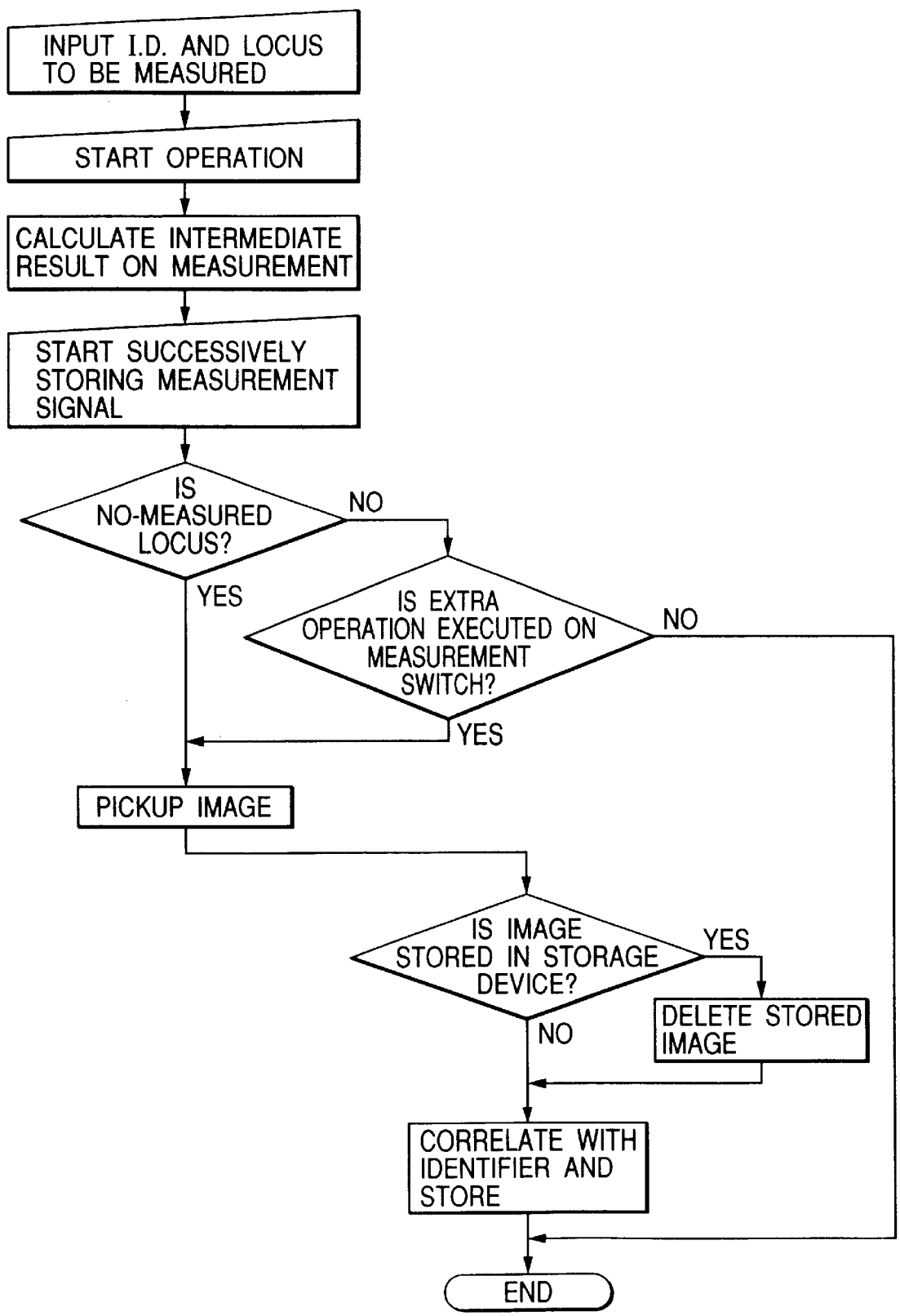
FIG. 2 is a flowchart representing operation of the system.

FIG. 2 is a flowchart showing apparatus operation from the start of measurement operation to the image storage. In the eye fundus blood flowmeter, the eye fundus of the same eye is measured in a plurality of positions. Also, the same locus is measured plural times during one measurement. Alternatively, a blood flow velocity and a change in volume of a blood flow are measured repeatedly for several days. Thus, it is necessary to manage measurement results for each patient, each of right and left eyes to be examined, and each measurement position. An example of processing which is performed by an operator is described below.

FIG. 3A is display examples of an input window for selecting a patient's ID or identity number, right and left eyes, and a locus name for measurement on the display 6. First, the operator inputs an ID of a patient to be measured (in this example, "abc201") to an input box 20 on the window. The registered patient's ID can be inputted using a pull-down menu. If the first measurement for the patient is to be performed, no examination result is stored in the memory 11 and, columns 21 for the right and left eyes, which are located in a lower portion of the screen, are displayed as blank columns. In this case, before the examination, the operator executes new registration. Using a window shown in FIG. 3B, an arbitrary character and name are inputted to an input box 22 with respect to the locus name for measurement. Next, an item representing either the right eye or the left eye is selected in a selection box 23, and an item representing either the artery or the vein is selected in a selection box 24. In the example of FIG. 3B, the locus name is inputted as "01", and the items representing the right eye (R) and the artery (A) are selected. Here, when a registration button 25 on an upper portion of the screen is pushed, the identifier "R01A" is registered. In the case of canceling of the registration, a cancel button 26 is pushed.

According to the registration, the determining circuit 10 determines the identifier "R01A" as a locus to be measured next. Since this position is a first measurement position, the discriminating circuit 8 determines that matter from data stored in the memory 11. In this case, as shown in the flowchart of FIG. 2, with respect to the first measurement position, image pickup is always performed after the measurement.

Viewing a finder of the eye fundus blood flowmeter 1, the operator operates the joystick and a focusing nob (not shown) of the operation device 2 to perform alignment and focusing. Then, when the push button of the operation device 2 is pushed to turn on the first-action switch, a light flux from a tracking light source is irradiated to the eye fundus. Further, while the push button for turning on the first-action switch is continuously pushed, light fluxes from a measurement light source together with the tracking light source are continuously irradiated to the eye fundus to execute the tracking.

FIG. 4 shows a state of the eye fundus in this case. The eye fundus image is taken and stored. Measurement light M and tracking light T are irradiated onto a target blood vessel V on the eye fundus. When the measurement light is rightly irradiated onto the target blood vessel V, signal lights received by two photomultipliers as light receiving devices which are arranged in a measurement optical system of the eye fundus blood flowmeter 1 and receive signal lights from a position to be measured in two directions, are outputted to the processor 5. The processor 5 intermittently (for example, each period of 10 ms) stores output signals successively outputted from the photomultipliers in a memory, as shown in FIG. 5. Then, the stored output signals are A/D-converted and performed with FFT (fast Fourier transform) processing to calculate FFT waveforms as intermediate results as shown in FIGS. 6A and 6B.

Here, when the operator pushes the push button of the operation device 2 for turning on the second-action switch, the blood flow measurement and the image pickup are started. The controller 4 stores output signals (eye fundus image information) from image pickup elements built in the eye fundus blood flowmeter 1, together with the successive output signals (blood flow velocity information) from the photomultipliers for a predetermined period. An image by the image pickup elements is obtained by superimposing images of the measurement light M and the tracking light T as information (marks) representing a measurement position on the eye fundus image, as shown in FIG. 4. This image is correlated with the identifier "R01A" and then stored in the storage device 7. Also, information representing that the measurement with respect to the identifier "R01A" has been performed is stored in the memory 11.

Figure 7A:
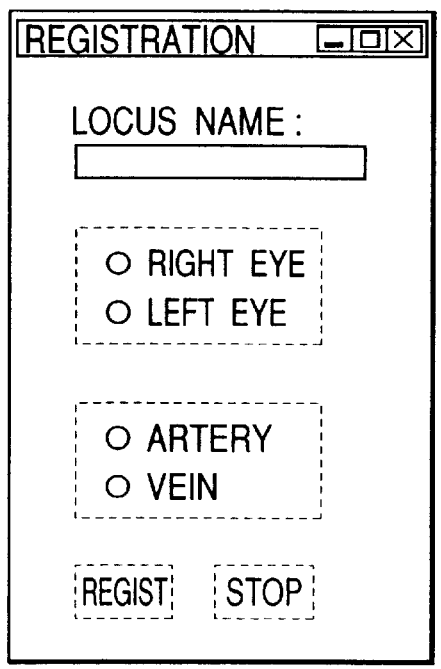
FIGS. 7A and 7B are screen display examples for inputting an examination locus.
Figure 7B:
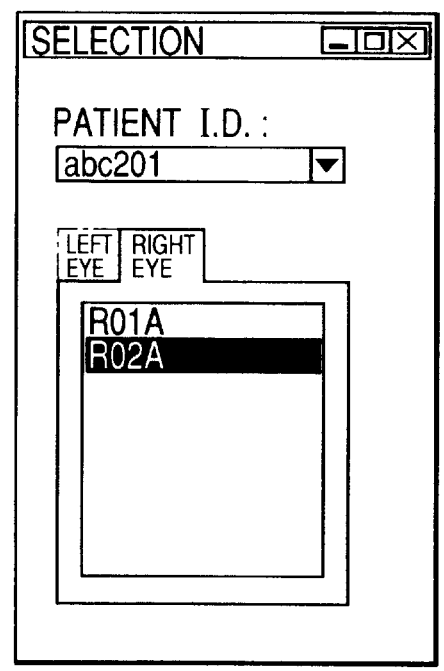

Subsequently, assuming that the operator desired to measure a blood flow velocity of other blood vessel. In an input window shown in FIG. 7A, the operator inputs the locus name "02", selects the items representing the right eye (R) and the artery (A), and pushes the registration button on the screen. Then, as shown in FIG. 7B, a new identifier "R02A" different from the above identifier is registered in the box column for the right eye. The determining circuit 10 determines that next measurement position is "R02A". The discriminating circuit 8 determines that the locus of "R02A" is a no-measured locus with reference to contents of the memory 11. Succeeding procedures for measurement and image pickup are similar to those in the case of the above-explained "R01A".

Here, assuming that the operator desired to again measure a blood flow velocity of a blood vessel with respect to the identifier "R01A" which has already been measured. In this case, as shown in FIG. 7B, the identifiers "R01A" and "R02A" which have already been measured are displayed on the box column for the right eye. The operator selects "R01A" of these identifiers. Then, the determining circuit 10 determines "R01A" as next measurement position. The discriminating circuit 8 determines that this locus is a locus which has already measured with reference to the contents of the memory 11. When the operator pushes the push button of the operation device 2 for turning on the first-action switch, the irradiation of the tracking beam is started. While the operator continuously pushes the push button for turning on the first-action switch, signal storing in blood flow measurement is executed. As described above, the processor 5 intermittently (for example, each period of 10 ms) stores output signals successively outputted from the photomultipliers in the memory, as shown in the time chart of FIG. 5. Then, the stored signals are A/D-converted and performed with FFT processing to calculate FFT waveforms as intermediate results as shown in FIGS. 6A and 6B.

Figure 8:
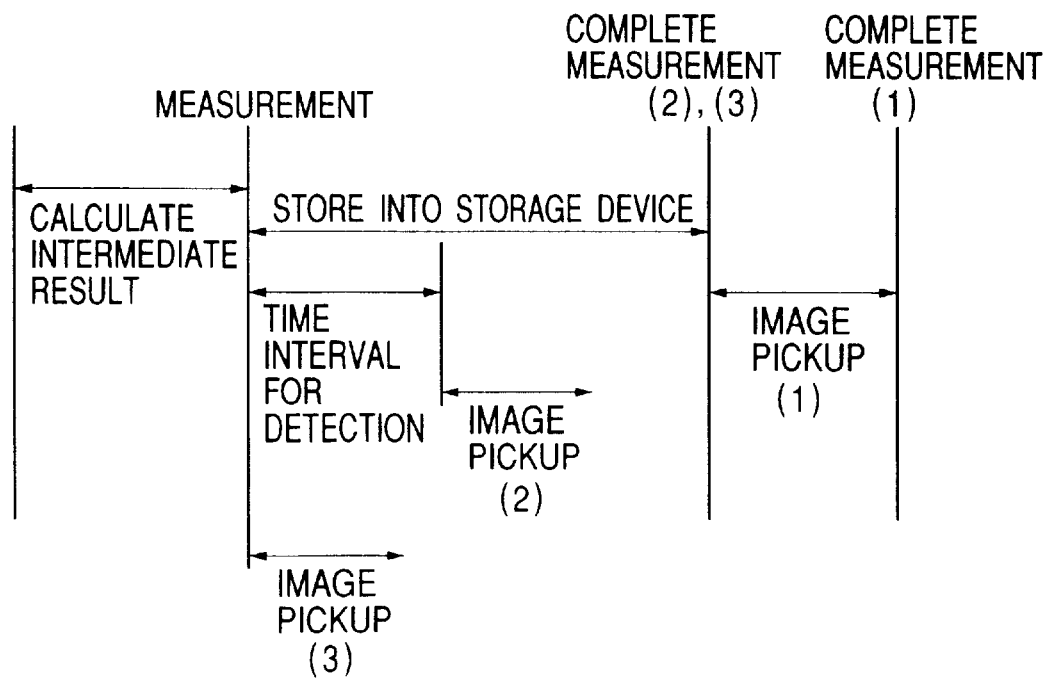
FIG. 8 is a time chart representing a sequence of signals during measurement.

Succeeding processing is different from that of the above explained example. That is, with the stage that the operator pushes the push button for turning on the second-action switch to start the blood flow measurement, whether the image pickup for the fundus of a patient is performed or not can be selected in accordance with the operator's will. When the image pickup is performed, the operator executes extra operation on the push button of the operation device 2 for turning on the second-action switch. Concretely, in the chart shown in FIG. 8, assuming that, the case where the push button for turning on the second-action switch is continuously pushed for a period longer than a predetermined period within a predetermined interval indicated as "a predetermined interval for input detection", corresponds to the extra operation, the image pickup is performed in accordance with this extra operation. On the other hand, assuming that, the case where a continuous button pushing period is shorter than the predetermined period, or the case where the continuous button pushing period is longer than the predetermined interval, corresponds to no extra operation. Thus, in this case, as shown in the flowchart of FIG. 2, the image pickup is canceled to record no image. The controller 4 measures a time that the push button for turning on the second-action switch is to be pushed. FIG. 8 is a time chart representing this sequence. A predetermined interval for detecting whether or not predetermined operation is performed by a measurement switch 10 is set in the controller 4. When the measured time is longer than a setting time within the predetermined interval, the image pickup is performed. The controller 4 stores the successive output signals (blood flow velocity information) from the photomultipliers for a predetermined period, and simultaneously performs control such that an image which the images of the measurement light M and the tracking light T are superimposed on the eye fundus image is obtained by the image pickup elements of the eye fundus blood flowmeter 1. The stored current image is overwritten in an image of the identical locus, which has already been stored, and stored in the storage device 7. That is, since the storage device 7 stores only one image for one measurement position (one identifier), if an image of the identical measurement position has already been stored, this image is canceled (overwritten) and then a new image is stored.

Incidentally, in this embodiment, as the extra operation for the push button for turning on the second-action switch, when the operator continuously pushes the button for a period longer than the predetermined period, the image pickup is executed. Otherwise the image pickup is canceled. However, there is another method in addition to such operation. For example, the following control may be performed. That is, when the operator once pushes the push button for turning on the second-action switch, the measurement is executed. Then, when the operator pushes the above button plural times in succession, the image pickup is executed. Otherwise the image pickup may be canceled. There is still another method. For example, the following control may be performed. That is, when the operator pushes the push button for turning on the second-action switch, the measurement is executed. Then, when the operator again pushes the above button within a predetermined period, the image pickup is executed. Otherwise the image pickup may be canceled. In any method, it is characterized in that whether the image pickup is executed or canceled is determined by the extra operation by the operator for the push button for turning on the second-action switch.

Also, with respect to timing of the start of the image pickup, there are three cases mentioned below.

(1) An eye fundus image pickup is started almost simultaneously with successive storing of output signals from the photomultipliers for a predetermined period and its storing completion. That is, the eye fundus image pickup is started almost simultaneously with the completion of storing of a measurement result into the storage device. This sequence is represented as "image pickup (1)" in FIG. 8.

(2) The image pickup is started during the measurement. That is, while a measurement result is stored in the storage device, eye fundus image pickup is started. This sequence is represented as "image pickup (2)" in FIG. 8.

(3) If first measurement for a locus is performed, image pickup is not canceled. In this case, output signals from the photomultipliers are stored, and the image pickup is started almost simultaneously with the start of this storing. That is, the eye fundus image pickup may be started almost simultaneously with the start of storing of a measurement result into the storage device. This sequence is represented as "image pickup (3)" in FIG. 8.

Here, some variation examples will be explained. In the above example, tracking is executed by using the first-action switch (first switch) of the double-action-switch as a trigger, the measurement is executed by using the second-action switch (second switch) as a trigger, and the image pickup is executed by the extra operation for the second switch. As other embodiment, an "image pickup execution switch" is separately provided on a panel near the operation device 2 (for example, in a position as represented by a dotted line 30 of FIG. 1). Thus, the tracking may be started by using the first-action switch of the double-action-switch as a trigger, the measurement may be executed (the image pickup is not performed) by using the second-action switch as a trigger, and the image pickup may be performed when the operator pushes the "image pickup execution switch". In this case, the operator operates the image pickup execution switch, so that whether the image pickup is executed or not can be determined. As a result, unnecessary image pickup can be prevented.

As a further variation example, the measurement may be executed by using the first-action switch of the double-action-switch as a trigger, and the image pickup may be executed by using the second-action switch as a trigger. In this case, the operator operates the second-action switch of the double-action-switch, so that whether the image pickup is executed or not can be determined. As a result, unnecessary image pickup can be prevented. In this case, an operation device for tracking may be separately provided. Alternatively, the tracking system itself can be omitted.

What is claimed is:

1. An ophthalmologic apparatus comprising:
   a measuring system for measuring an eye fundus of an eye to be examined;
   an image pickup system for performing image pickup of the eye fundus together with information representing a measurement position in the measuring system;
   a switch operable by an operator; and
   a control system for controlling said measuring system to start measurement in response to a first operation of the switch as a trigger, and then controlling said image pickup system to execute the image pickup in response to a second operation of the switch, and otherwise not to execute the image pickup.

2. An ophthalmologic apparatus according to claim 1, wherein the switch has a push button, and the control system controls:
   to execute the measurement when the operator pushes the push button; and then
   to execute the image pickup when the operator continuously pushes the push button for a period longer than a predetermined period, otherwise to cancel the image pickup.

3. An ophthalmologic apparatus according to claim 1, wherein the switch has a push button, and the control system controls:
   to execute the measurement when the operator pushes the push button once; and then
   to execute the image pickup when the operator pushes the push button plural times in succession, otherwise to cancel the image pickup.

4. An ophthalmologic apparatus according to claim 1, wherein the switch has a push button, and the control system controls:
   to execute the measurement when the operator pushes the push button; and then
   to execute the image pickup when the operator again pushes the push button within a predetermined period, otherwise to cancel the image pickup.

5. An ophthalmologic apparatus according to claim 1, wherein the switch comprises a first switch and a second switch in the form of a double-action-switch in which the first switch and the second switch are turned on in order by a single push button.

6. An ophthalmologic apparatus according to claim 1, wherein the measuring system includes a tracking system for performing tracking of the blood vessel, and the information representing the measurement position is an image of, a measurement beam or a tracking beam.

7. An ophthalmologic apparatus according to claim 1, further comprising:
   a registering system for registering an identifier inherent to each measurement position; and
   a storage device for storing an image of the eye fundus, which is taken by the image pickup system, in relation to the identifier.

8. An ophthalmologic apparatus according to claim 7, wherein the storage device stores the taken image together with a measurement result measured by the measuring system, in relation to the identifier.

9. An ophthalmologic apparatus comprising:
   a measuring system for measuring an eye fundus of an eye to be examined;
   an image pickup system for performing image pickup of the eye fundus together with information representing a measurement position in the measuring system;
   a switch operable by an operator; and
   a control system for controlling said measuring system to execute measurement and the image pickup system to execute image pickup using operation of the switch by the operator as a trigger, the control system controlling said apparatus to cancel the image pickup in some cases.

10. An ophthalmologic apparatus according to claim 9, wherein the control system does not perform cancellation of the image pickup when a measurement position is taking a first measurement, otherwise the control system performs cancellation of the image pickup.

11. An ophthalmologic apparatus according to claim 9, wherein the control system controls to execute the image pickup when the operator operates extra operation for the switch, otherwise the control system cancels the image pickup.

12. An ophthalmologic apparatus according to claim 11, wherein the control system does not cancel the image pickup when a measurement position is for first measurement.

13. An ophthalmologic apparatus according to claim 9, wherein the measuring system includes a tracking system for performing tracking of the blood vessel, and the information representing the measurement position is an image of a measurement beam or a tracking beam.

14. An ophthalmologic apparatus according to claim 9, further comprising:
   a registering system for registering an identifier inherent to each measurement position; and
   a storage device for storing an image of the eye fundus, which is taken by the image pickup system, in relation to the identifier.

15. An ophthalmologic apparatus according to claim 14, wherein the storage device stores the taken image together with a measurement result measured by the measuring system, in relation to the identifier.

16. An ophthalmologic apparatus comprising:
   a measuring system for measuring an eye fundus of an eye to be examined;
   an image pickup system for performing image pickup of the eye fundus together with information representing a measurement position in the measuring system;
   a registering system for registering an inherent identifier corresponding to a measurement position; and
   a storage device for storing an image of the eye fundus, which is taken by the image pickup system, in relation to the identifier,
   wherein the storage device stores the image of the eye fundus together with a measurement result measured by the measuring system, in relation to the identifier.

17. An ophthalmologic apparatus according to claim 16, wherein when a plurality of image pickups are performed, the storage device deletes a preceding image and stores a current image.

18. An ophthalmologic apparatus according to claim 16, wherein while the measurement result by the measuring system is stored in the storage device, the image pickup of the eye fundus is started.

19. An opthalmologic apparatus according to claim 16, wherein the image pickup of the eye fundus is started almost simultaneously with a start storing of the measurement result by the measuring system into the storage device.

20. An ophthalmologic apparatus according to claim 16, wherein the image pickup of the eye fundus is started almost simultaneously with completion of storing of the measurement result by the measuring system into the storage device.

* * * * *

UNITED STATES PATENT AND TRADEMARK OFFICE
CERTIFICATE OF CORRECTION

PATENT NO. : 6,598,970 B2
DATED : July 29, 2003
INVENTOR(S) : Hiroshi Itoh

It is certified that error appears in the above-identified patent and that said Letters Patent is hereby corrected as shown below:

<u>Column 10,</u>
Line 54, "opthalmologic" should read -- ophthalmologic --.

Signed and Sealed this

Third Day of February, 2004

JON W. DUDAS
*Acting Director of the United States Patent and Trademark Office*